United States Patent
Rossignol-Castera et al.

(10) Patent No.: US 10,532,023 B2
(45) Date of Patent: *Jan. 14, 2020

(54) CAMELLIA JAPONICA EXTRACT AND COSMETIC COMPOSITIONS CONTAINING SAME

(71) Applicant: CHANEL PARFUMS BEAUTE, Neuilly sur Seine (FR)

(72) Inventors: Anne Rossignol-Castera, Restinclieres (FR); Annabelle L'Hermitte, Montpellier (FR); Gaelle Gendronneau, Chaumes-en-Brie (FR); Serge Holderith, Vicennes (FR); Yannick Maestro, Mouans Sartoux (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 373 days.

This patent is subject to a terminal disclaimer.

(21) Appl. No.: 15/500,624

(22) PCT Filed: Aug. 1, 2014

(86) PCT No.: PCT/FR2014/052013
§ 371 (c)(1),
(2) Date: Jan. 31, 2017

(87) PCT Pub. No.: WO2016/016515
PCT Pub. Date: Feb. 4, 2016

(65) Prior Publication Data
US 2017/0216194 A1    Aug. 3, 2017

(51) Int. Cl.
*A61K 36/82* (2006.01)
*A61K 8/97* (2017.01)
*A61Q 19/00* (2006.01)
*C11B 1/10* (2006.01)
*A61K 8/73* (2006.01)
*A61K 8/99* (2017.01)

(52) U.S. Cl.
CPC ............... *A61K 8/97* (2013.01); *A61K 8/735* (2013.01); *A61K 8/99* (2013.01); *A61Q 19/00* (2013.01); *A61Q 19/007* (2013.01); *C11B 1/10* (2013.01); *A61K 2800/805* (2013.01); *A61K 2800/82* (2013.01)

(58) Field of Classification Search
CPC ...................................... A61K 36/82
See application file for complete search history.

(56) References Cited

U.S. PATENT DOCUMENTS 8,715,651 B2 * 5/2014 Maestro ............ A61K 8/97
424/115
2012/0282244 A1  11/2012  Maestro et al.
2013/0146481 A1   6/2013  Koganov

FOREIGN PATENT DOCUMENTS

| FR | 2 943 684 A1 | 10/2010 |
| KR | 2009 0107128 A | 10/2009 |
| WO | 2010/112760 A1 | 10/2010 |
| WO | 2011/083110 A2 | 7/2011 |

OTHER PUBLICATIONS

International Search Report, dated Apr. 28, 2015, from corresponding PCT application.

* cited by examiner

*Primary Examiner* — Rosanne Kosson
(74) *Attorney, Agent, or Firm* — Young & Thompson

(57) ABSTRACT

Disclosed is a Japanese *camellia* extract, obtained by extracting *Camellia japonica* flowers by way of a fatty substance or fatty substance mixture, and to a cosmetic composition including one such extract that has, in particular, a skin-moisturizing effect.

20 Claims, No Drawings

CAMELLIA JAPONICA EXTRACT AND COSMETIC COMPOSITIONS CONTAINING SAME

BACKGROUND OF THE INVENTION

1. Field of the Invention

The subject of the present invention is a *Camellia japonica* flower extract, characterized in that it can be obtained by extracting the flowers by means of at least one fatty substance, and also the use thereof in the cosmetics industry, for moisturizing and/or protecting human skin against drying out.

2. Description of the Related Art

The skin mainly consists of three layers, namely, starting from the most superficial, the epidermis, the dermis and the hypodermis.

The epidermis consists in particular of keratinocytes (which are in the majority), melanocytes (involved in skin pigmentation) and Langerhans cells. Its function is to protect the body against the outside environment and to ensure its integrity, in particular to slow down the penetration of microorganisms or of chemical substances, and to prevent evaporation of the water contained in the skin.

To do this, the keratinocytes undergo a continuous oriented maturation process through which the keratinocytes located in the basal layer of the epidermis form, at the terminal stage of their differentiation, corneocytes which are completely dead cells keratinized in the form of cornified envelopes consisting of proteins and lipids such as ceramides. During this differentiation process, intercorneocyte epidermis lipids are also formed and then organized in the form of bilayers (sheets) in the stratum corneum. They participate, with the abovementioned cornified envelopes, in the barrier function of the epidermis.

The barrier function of the epidermis can however be disrupted under certain climatic conditions (under the effect of cold and/or wind, for example), or else under the effect of stress or fatigue, in particular, thus promoting the penetration of allergens, of irritant agents or of microorganisms which thus bring about drying out of the skin capable of generating feelings of discomfort such as tautness or redness, and also of detrimentally modifying the radiance of the complexion and the suppleness of the skin.

In order to prevent this phenomenon or to correct it, it is known to apply to the skin cosmetic compositions containing hygroscopic agents, such as sugars or polyols, intended to capture the water present in the skin and thus slow down its evaporation. Moreover, these compositions frequently incorporate active agents which act on one or more of the various biological targets involved either in skin regeneration process, in particular in keratinocyte differentiation, epidermal lipid synthesis and corneocyte cohesion, or in the endogenous synthesis of constituents of natural moisturizing factor (NMF) of the skin, in particular in the synthesis of proteoglycans.

Examples of such active agents are in particular α- and β-hydroxyl acids, in particular lactic acid, glycolic acid and salicylic acid, urea or aminosulfonic compounds.

However, there still remains the need to provide novel cosmetic active agents that allow more effective moisturization of the skin.

In addition, given the ever increasing search by consumers for natural products containing as few synthetic ingredients as possible, and the increasingly extensive regulatory constraints affecting compounds derived from the chemical industry, it would be desirable for these cosmetic active agents to be of plant origin.

The applicant has already shown, in its international application WO 2011/083110, that it is possible to effectively combat drying out of the skin using an aqueous-alcoholic extract of *camellia*, the latter acting by stimulating the expression of HSP32 mRNA, stimulating the expression of the HSP27 protein and stimulating the expression of the PPAR-β/δ protein on the keratinocytes treated. The applicant has also described an extraction process in its international application WO 2010/112760.

However, since the extracts of the type of those described in application WO 2011/083110 are carried in an aqueous-alcoholic medium, they are not suitable for all cosmetic applications, in particular when the desired compositions are anhydrous or have a continuous fatty phase. Furthermore, some alcohols, such as ethanol or methanol, for preparing the extract can prove to be drying for the skin, which goes against the effect initially desired.

Oily extracts of *camellia* have already been proposed, such as the refined *camellia* oil sold by the company Ardex, produced from the variety *Camellia oleifera*. However, these oily extracts, although they are effective for preventing drying out of the skin generated by the use of alcohols, surprisingly show no effect in terms of improving skin moisturization.

BRIEF SUMMARY OF THE INVENTION

It is thus to the applicant's credit to have developed an oily extract of *Camellia japonica* flower which does not have the drawbacks of the aqueous-alcoholic extracts currently on the market, while at the same time preserving, or even improving, their moisturizing action on the skin by stimulating the expression of the KRT2 (keratin 2) gene.

A subject of the present invention is thus, according to a first aspect, a *Camellia japonica* flower extract obtainable by means of an extraction process comprising the following steps:

a) mixing and impregnation of a *Camellia japonica* flower powder with a fatty substance or a fatty substance mixture at a temperature above the melting point of said fatty substance or of said mixture and under an atmosphere free or essentially free of oxygen, b) microdispersion of the *Camellia japonica* flower powder in the fatty substance or said fatty substance mixture at a temperature above the melting point of said fatty substance or of said mixture, under an atmosphere free or essentially free of oxygen, c) heating of the mixture thus obtained at a temperature of between 60 and 180° C. for a period of between 1 and 10 minutes, under an atmosphere free or essentially free of oxygen, it being possible for step c) to be carried out before, during or after step b).

According to one essential feature of the invention, steps a), b) and c) of the process for preparing the oily extract of *Camellia japonica* are carried out in an atmosphere free or essentially free of oxygen. This means that the work is carried out under gas or an inert atmosphere or under a vacuum or partial vacuum. The residual oxygen content must be sufficiently low so as not to cause oxidation reactions sensitive to the temperature of the heat treatment. These steps can thus be carried out under an inert atmosphere, for example under nitrogen and preferably under continuous nitrogen flushing, allowing extraction of the oxygen present or capable of forming. A closed reactor can be used with continuous extraction of the oxygen by means of a nitrogen stream. It is also possible to perform nitrogen sparging, combined with the nitrogen stream, at least at the beginning of the heat treatment. These steps can also be carried out under vacuum. Performing the process in this manner thus confers an additional advantage, namely the entrainment of the volatile materials with a deodorizing effect on the mixture.

A subject of the invention is also, according to a second aspect, a cosmetic composition comprising, in a physiologically acceptable medium, at least one *Camellia japonica* flower extract as described above.

Finally, a subject of the present invention, according to a third aspect, is the cosmetic use of said extract or of said composition for moisturizing human skin.

DETAILED DESCRIPTION OF THE INVENTION

The *camellia* extract used in the context of the present invention has the advantage of being a lipid extract, and in particular an oily extract, which gives it an improved skin-moisturizing effect.

In the context of the present invention, the *Camellia japonica* flower extract can be obtained by means of an extraction process comprising a step a) of mixing and impregnation of a *Camellia japonica* flower powder with a fatty substance or a fatty substance mixture at a temperature above the melting point of said fatty substance and under an atmosphere free or essentially free of oxygen.

*Camellia* is a genus of flowering plants of the family Theaceae, originating from East and South-East Asia from the Himalaya chain to Japan and in Indonesia. *Camellia* flowers are recognized, inter alia, for their antibacterial, antioxidant, anti-inflammatory, astringent and tonic properties. The number of species included in the genus differs depending on the botanist, and varies between 100 and 250 species. Mention may in particular be made of the white-colored flowers, in particular the variety Alba plena, very dark red-colored *Camellia japonica* flowers of the chocolate red to black red type, in particular the varieties Black magic, Kuro tsubaki, Black Domino, Koronkoku, Kon wabisuke, Kuro wabisuke, Murasaki-no-ue, and Sir Victor Davis, and hybrid *camellia* flowers of Kuro Tsubaki, the variety names of which are Night Rider or Black Opal. The Black Magic and Night Rider varieties are the most common *Camellia japonica* varieties in France. The colors of *camellia* flowers can vary according to the pH and to the metals and metalloids present in the soil or substrate. Camellias generally flower from mid-February to April. It is however possible to obtain flowers as early as October by means of hormonal treatment.

The extract according to the invention is obtained from the flower of *Camellia japonica*, and preferably from the white-colored flowers, in particular of the variety Alba plena. Preferably, the *Camellia japonica* flowers used in the invention are grown in France.

The *Camellia japonica* flower extract is preferably in the form of a dispersible powder. The term "dispersible" is intended to mean that the *Camellia japonica* flower powder is in a dissociated form capable of being finely dispersed, and for example, the starting material is in particulate form and preferably pulverulent form. Fresh *Camellia japonica* flowers are for example firstly isolated from the stems and then opened and placed flat on racks. They are then dehydrated under mild conditions, either at ambient temperature in the dark or in a ventilated drier at a temperature below 35° C. The flowers are preferably dried until a solids content greater than 80% and preferentially greater than 85% is obtained.

The flowers are then reduced to dispersible powder by any milling process conventionally known to those skilled in the art, for example at ambient temperature in a knife mill or, according to one preferred embodiment, by low-temperature milling. For low-temperature milling, the flowers are preferably cooled to −80° C. and immediately milled in a propeller mixer at a temperature of between −20 and −80° C., so as to obtain a fine and even powder. The cryopreservation advantageously makes it possible to ensure better preservation of the moisturizing properties of the molecules contained in the flowers.

Preferably, the dispersible powder of *Camellia japonica* flowers used for preparing the extract according to the invention has a mean particle size of less than 500 μm, preferentially less than 300 μm. The *Camellia japonica* flower powder has a mild floral odor and a color ranging from creamy white to brownish red.

The fatty substance(s) used in the process for preparing the *Camellia japonica* extract according to the invention are preferably natural or of natural origin. Among the natural fatty substances, use may in particular be made of refined plant oils comprising less than 0.1% of water by weight or of virgin or unrefined plant oils that may contain from 0.1% to 2% of water by weight, preferably from 0.1% to 0.3% of water by weight.

In particular, the fatty substance used as extraction solvent is preferentially of plant origin, and may be a plant oil that is liquid at ambient temperature (20-25° C.), a plant butter having a melting point of between 25 and 40° C., or a plant wax having a melting point above 40° C. According to one preferred embodiment, the fatty substance used as extraction solvent is a plant oil that is liquid at a temperature below ambient temperature, and in particular liquid at a temperature of approximately 20° C.

By way of example of oils that can be used for obtaining the extract according to the invention, mention may be made of *camellia* oil, rapeseed oil, sunflower oil, olive oil, sesame oil, apricot kernel oil, grape seed oil, sweet almond oil, safflower oil, hazelnut oil, argan oil, rose musk oil, evening primrose oil, borage oil, jojoba liquid wax, and mixtures thereof. An oil which is a source of omega 6 or omega 3 polyunsaturated fatty acids that can play a positive role on membrane fluidity and on skin moisturization will preferentially be chosen.

According to one embodiment of the invention, the ratio between the *Camellia japonica* flower powder and the fatty substance in step a) is between 1:0.5 and 1:20, preferably between 1:19 and 1:1, and more preferentially between 1:9 and 1:3, said ratio being expressed by weight/weight of fatty substance or by weight/volume of fatty substance.

Step a) is carried out at a temperature above or equal to the melting point of the fatty substance or of the fatty substance mixture used. In particular, the temperature is advantageously between this melting point and the melting point +20° C., preferably +10° C. Ambient temperature (20-25° C.) is perfectly suitable for fatty substances such as oils that are liquid at this temperature. The duration of step a) can be between 1 and 48 hours, preferably between 5 and 40 hours, more preferentially between 12 and 36 hours, even more preferentially between 20 and 30 hours, and, according to one particularly preferred embodiment, the duration of impregnation step a) is approximately 24 hours.

Step a) is carried out under an atmosphere free or essentially free of oxygen, and preferably under a nitrogen-saturated atmosphere.

The process which makes it possible to obtain the extract according to the invention also comprises a step b) of microdispersion of the *Camellia japonica* flower powder in the fatty substance at a temperature above the melting point of said substance, under an atmosphere free or essentially free of oxygen.

This step b) allows not only the microdispersion of the *camellia* powder to be extracted, but also, on cell tissues, the breaking of the cells, thereby promoting the dispersion of the extracted molecules in the natural fatty substance. This effect can be obtained by treating the mixture by ultrasonic cavitation. The cavitation and dispersion under ultrasonic waves are preferably carried out in a closed reactor equipped with an ultrasound generator at low cavitation frequency, in particular less than 100 kHz and preferably of about from 20 to 30 kHz.

The duration of the ultrasound treatment is in particular between 2 and 30 minutes, preferably between 10 and 20 minutes.

Step b) is advantageously carried out at ambient temperature or at a temperature above the melting point of the fatty substance(s) used. The temperature is advantageously between this melting point and the melting point +20° C., preferably +10° C. Ambient temperature (20-25° C.) is perfectly suitable for oils that are liquid at this temperature.

The process for obtaining the *camellia* flower extract according to the invention also comprises a step c) of heating of the mixture, obtained in step a) or b), of said *Camellia japonica* flower powder with said fatty substance(s) at a temperature of between 80 and 180° C. for a period of between 1 and 10 minutes, under an atmosphere free or essentially free of oxygen.

In one preferred embodiment, the temperature of step c) is between 100 and 150° C., preferably between 110 and 130° C.

The heating step c) is carried out for a very short period ranging from 1 to 10 minutes, preferably from 1 to 5 minutes, and more preferentially from 1 to 3 minutes, this period corresponding to the time for which the treatment temperature is maintained once this temperature has been reached. The temperature increase time is also very short, in particular less than or equal to 5 minutes, preferably for 1 to 5 min., and more preferentially from 1 to 3 minutes.

Any rapid thermal heating system can be used, and in one preferred embodiment, the heat treatment is provided by microwaves. The use of a microwave source in a closed reactor makes it possible to reach the desired temperatures in a very short time. The heating at high temperature makes it possible, moreover, to increase the dissolving capacity of the fatty substance used and promotes contact between the *camellia* flower powder and said fatty substance, thus favoring the extraction yield. According to one preferred embodiment, the microwave generator used for the heating of step c) has a working power ranging from 500 to 10 000 watts per kilogram of mixture, preferably of about 700 to 1500 watts per kilogram of mixture, and more preferentially of about 1000 watts per kilogram of mixture.

According to one advantageous feature, an oxygen-trapping or oxygen-reducing compound is added during step c) or just before. It is thus possible to add vitamin C, in the form of pure ascorbic acid, or of a salt such as sodium ascorbate or ascorbyl palmitate, citric acid or lactic acid in free or ester form, or lecithins, or else a combination of these compounds. An individual amount of from 0.01% to 1% by weight in the mixture, preferentially from 0.1% to 0.5% by weight in the mixture, will be added.

Steps a), b) and/or c) are advantageously carried out in the absence of light or of any oxidizing radiation such as UV radiation, so as to limit the risks of photooxidation and of degradation of the photosensitive molecules.

Steps a), b) and/or c) can be carried out with or without stirring of the mixture and preferentially with stirring.

According to one embodiment, the process consists of a combined sequence of steps a), b) and c), the order of steps b) and c) being of no consequence, each step being carried out a minimum of once each.

Steps b) and c) can in particular be carried out simultaneously. According to one preferred embodiment, steps b) and c) are carried out at least a second time and for example n times; they then correspond to steps bn) and cn), n corresponding to the total number of repetitions of the cycle {(step a)+(step b)}, n being at least equal to 2, preferably n being equal to 2.

In one embodiment, a period of passive diffusion of the compounds extracted in the oil and of cooling, optionally with gentle stirring, in a closed system under an atmosphere free or essentially free of oxygen, can be carried out between each step or after the final step.

The duration of this step must be sufficient for good diffusion of the active agents in the oil. This duration may in particular be between 1 h and 12 h, preferably between 1 h and 5 h. The cooling can be carried out in any known manner, in particular by passive cooling or using cooling means. This cooling step is advantageously carried out in an atmosphere free or essentially free of oxygen, like steps a), b) and c). It is advantageously carried out in the absence of light or of any oxidizing radiation such as UV radiation.

Finally, the process may comprise one or more step(s) of clarification for the oily extract. The term "clarification" is intended to mean all the mechanical separations known to those skilled in the art. It can for example be chosen from filtration, decanting, centrifugation, spin-filtering, or a combination of these techniques. Preferably, the separation is carried out by centrifugation or filtration. This separation step can be carried out at a temperature of between 40 and 60° C. in a centrifuge equipped with a filtering cloth which has a porosity of less than 10 μm and preferentially less than 5 μm and at a speed greater than 2500 revolutions/min.

The clarification steps make it possible to obtain a product which is both substantially clear to the eye and free of microparticles in suspension.

According to one preferred embodiment, the *Camellia japonica* extract according to the present invention can be obtained by means of the process described above, according to steps a), bn), optionally a diffusion/cooling step, cn), optionally another diffusion/cooling step, a), and a final step of separation.

The *Camellia japonica* flower extract that can be obtained by means of the process according to the invention has a high concentration of active agents and can be in the form of an oily solution, an oily microdispersion, an oily microsuspension or an oily microemulsion, said form being stable over time. In particular, the extract according to the invention is in the form of an oil which is transparent to the eye, shiny, homogeneous, and light yellow to orangey yellow in color.

The *Camellia japonica* flower extract is used according to the invention for cosmetic purposes, for moisturizing human skin or protecting it against drying out. It can also be used for combating the skin signs resulting from a disruptive barrier function, including roughness of the skin, discomfort, including redness, tautness, tingling and itching, loss of radiance of the complexion or a dull complexion, loss of suppleness of the skin, and cracks.

The moisturizing effect of the composition used according to the invention can in particular be observed through an increase in the expression of the keratin 2 (KTR2) gene, according to usual techniques well known to those skilled in the art.

A subject of the invention is also a cosmetic composition comprising a *Camellia japonica* flower extract as described above.

Preferably, the composition according to the invention, containing the *Camellia japonica* flower extract, is applied to dry, preferably nonpathological, skin. It can be advantageously applied to the skin of the face, of the neck and optionally of the neckline or, as a variant, to any part of the body. The composition containing this extract can be applied in the morning and/or the evening, to the whole of the face, of the neck and optionally of the neckline, or even of the body.

The composition used according to the invention generally comprises, in addition to the extract described above, a physiologically acceptable and preferably cosmetically acceptable medium, that is to say one which is suitable for use in contact with human skin without any risk of toxicity, incompatibility, instability or allergic response and in particular which does not cause sensations of discomfort (redness, tautness, tingling, etc.) unacceptable for the user.

This medium generally contains water and optionally other solvents such as oils.

The composition used according to the invention can be in any form suitable for topical application to the skin and in particular in the form of an anhydrous formulation, an oil-in-water, water-in-oil or optionally multiple (W/O/W or O/W/O) emulsion, which can optionally be microemulsions or nanoemulsions, or in the form of a powder. This composition is preferably in the form of an oil-in-water emulsion.

This composition is preferably used as a product for caring for or cleansing the skin of the face and/or of the body and it can in particular be in the form of a fluid, a gel or a foam, packaged for example in a pump-dispenser bottle, an aerosol or a tube, or a cream packaged for example in a pot. As a variant, it can have the form of a makeup product and in particular of a foundation or a loose or compact powder.

In addition to the *Camellia japonica* flower extract described above, the composition according to the invention can also comprise at least one additive which is customary in the cosmetics field, such as for example at least one compound chosen from a gelling agent and/or thickener, a surfactant or co-surfactant, a liquid fatty substance or an oil, a wax, a silicone elastomer, a sunscreen, a dye, a matting agent or a filler, a pigment, a tensioning agent, a preservative, a sequestrant agent, a fragrance, and mixtures thereof.

In particular, the composition according to the invention can contain, in a non-limiting manner, one or more of the following additives:

one or more aqueous-phase gelling agent(s) and/or thickener(s), chosen for example from hydrophilic or amphiphilic, crosslinked or non-crosslinked homopolymers and copolymers of acryloylmethylpropanesulfonic acid (AMPS) and/or of acrylamide and/or of acrylic acid and/or of acrylic acid salts or esters, such as ammonium acryloyldimethyltaurate/VP copolymer and ammonium acryloyldimethyltaurate/beheneth-25 methacrylate copolymer, in particular those sold under the names Aristoflex® AVC and HMB from Clariant, or else the acrylates/C10-30 alkyl acrylate crosspolymer sold under the trade name Pemulen® TR-1 or TR-2, Carbopol® 1382, Carbopol® Ultrez 20 by the company Novéon, cellulose-based derivatives, gums of plant origin (acacia gum or gum Arabic, agar, guar, locust bean, alginates, carrageenans, pectin), or of microbial origin (xanthan, pullulan), or clays (laponite). Said gelling agent and/or thickener can be present in the composition in a content of about from 0.01% to 5% by weight, relative to the total weight of the composition;

one or more surfactant(s), preferably emulsifying surfactant(s), whether they are non-ionic, anionic, cationic or amphoteric, and in particular esters of fatty acids and of polyols, such as oxyalkylenated (more particularly polyoxyethylenated) esters of fatty acids and of glycerol, oxyalkylenated esters of fatty acids and of sorbitan, oxyalkylenated (oxyethylenated and/or oxypropylenated) fatty acid esters, for instance the PEG-100 stearate/glyceryl stearate mixture sold for example by the company Croda Inc. under the name Arlacel® 165 and esters of fatty acids and of sucrose, for instance sucrose stearate; ethers of fatty alcohol and of sugar, in particular alkylpolyglucosides (APGs) such as decylglucoside and laurylglucoside sold for example by the company Henkel under the respective names Plantaren® 2000 and Plantaren® 1200, cetostearyl glucoside optionally as a mixture with cetostearyl alcohol, sold for example under the name Montanov® 68 by the company SEPPIC, and also arachidyl glucoside, for example in the form of the mixture of arachidyl and behenyl alcohols and of arachidyl glucoside sold under the name Montanov® 202 by the company SEPPIC; ethers of fatty alcohols and of polyethylene glycol; polysiloxane modified polyethers; betaine and derivatives thereof; polyquaterniums; ethoxylated fatty alcohol sulfate salts; sulfosuccinates; sarcosinates; alkyl and dialkyl phosphates and salts thereof; and fatty acid soaps. Said surfactant can be present in the composition in a content of about from 0.1 to 8%, preferably 0.5 to 3% by weight, relative to the total weight of the composition;

one or more co-surfactant(s), such as linear fatty alcohols with a long carbon-based chain ($C_{14}$-$C_{20}$) and in particular cetyl and stearyl alcohols, said surfactant being present in the composition in a proportion of from 0.1% to 5%, preferably 0.5% to 2% by weight, relative to the total weight of the composition;

one or more fatty substance(s) that are liquid at ambient temperature, commonly referred to as volatile or non-volatile, hydrocarbon-based or silicone oils, which are linear, cyclic or branched, for example silicone oils such as polydimethylsiloxanes (dimethicones), polyalkylcyclosiloxanes (cyclomethicones) and polyalkylphenylsiloxanes (phenyl dimethicones); synthetic oils such as fluoro oils, alkyl benzoates and branched hydrocarbons such as polyisobutylene or isododecane; mineral oils (paraffin); plant oils (sweet almond oil, macadamia oil, blackcurrant oil, jojoba oil or else camelina *sativa* oil, such as the oil sold under the trade name Lipex® Omega 3/6 by the company Unipex); fatty alcohols, fatty amides, fatty acids or esters, for instance the $C_{12}$-$C_{15}$ alkyl benzoate sold under the trade name Finsolv® TN by the company Innospec or else the isononyl isononanoate sold under the trade name Wickenol® 151 by the company Alzo Inc., octyl palmitate, isopropyl lanolate, triglycerides including those of capric/caprylic acids, the dicaprylyl carbonate sold under the name Cetiol® CC by the company Cognis;

preferably in a proportion of from 0.1% to approximately 10%, preferably from 0.5% to 5% by weight, relative to the total weight of the composition;

one or more waxes (compound that is solid or substantially solid at ambient temperature, and the melting point of which is generally above 35° C.), such as ozokerite, polyethylene wax, beeswax or carnauba wax, preferably in a proportion of from 0.01% to approximately 5%, preferably 0.5% to 5% by weight, relative to the total weight of the composition;

one or more silicone elastomer(s) obtained in particular by reaction, in the presence of a catalyst, of a polysiloxane having at least one reactive group (hydrogen or vinyl, in particular) and bearing at least one end and/or side alkyl (in particular methyl) or phenyl group, with an organosilicone such as an organohydrogenopolysiloxane, preferably in a proportion of from 0.1% to approximately 20%, preferably 0.25% to 15% by weight, relative to the total weight of the composition;

one or more sunscreen(s), in particular organic screens, such as dibenzoylmethane derivatives (including the butyl methoxydibenzoylmethane sold in particular by DSM under the trade name Parsol® 1789), cinnamic acid derivatives (including the ethylhexyl methoxycinnamate sold in particular by DSM under the trade name Parsol® MCX), salicylates, para-aminobenzoic acids, β,β'-diphenyl acrylates, benzophenones, benzylidenecamphor derivatives, phenylbenzimidazoles, triazines, phenylbenzotriazoles and anthranilic derivatives; or inorganic screens, based on mineral oxides in the form of coated or uncoated pigments or nanopigments, and in particular based on titanium dioxide or zinc oxide; preferably in a proportion of from 0.1% to approximately 30%, better still from 0.5% to 20% by weight, relative to the total weight of the composition;

one or more water-soluble dye(s), such as, for example, the disodium salt of ponceau, the disodium salt of alizarin green, quinoline yellow, the trisodium salt of amaranth, the disodium salt of tartrazine, the monosodium salt of rhodamine, the disodium salt of fuchsin or xanthophyll, preferably in a proportion of from 0.1% to approximately 2% by weight, relative to the total weight of the composition;

one or more fillers, in particular matting agents or soft-focus effect fillers, and in particular soft-focus effect powders.

The term "filler" should be understood to mean lamellar or non-lamellar, mineral or synthetic, colorless or white particles suitable for giving the composition body and stiffness and/or softness, a matt effect and uniformity immediately on application. These fillers can in particular modify or even mask wrinkles by means of a camouflage effect, or a soft-focus effect.

The matting agents can be chosen from matting polymers (in solution, in dispersion or particle form) and inorganic particles which reduce the shininess of the skin and unify the complexion.

The matting agent may in particular be chosen from a starch, talc, cellulose microbeads, plant fibers, synthetic fibers, in particular polyamide fibers (Nylon® powders such as Nylon-12 (Orgasol® sold by the company Atochem)), microspheres or acrylic copolymers in particular of polymethyl (meth)acrylate PMMA particles or the Micropearl® M310 particles sold by the company SEPPIC), silica powders, silicone resin powders, acrylic polymer powders, polyethylene powders, elastomeric crosslinked organopolysiloxanes (sold in particular under the name KSG® by the company Shin-Etsu, under the names Trefil®, BY29® or EPSX® by the company Dow Corning or under the name Gransil® by the company Grant Industries), talc/titanium dioxide/alumina/silica composite powders, silicate powders, and mixtures thereof.

The "soft-focus" effect filler may give the complexion transparency and a soft-focus effect. Preferably, the "soft-focus" fillers have a mean particle size of less than or equal to 30 microns, more preferentially less than or equal to 15 microns. These "soft-focus" fillers can be of any shape and in particular can be spherical or nonspherical. They can be chosen from powders of silica and silicates, in particular of alumina, powders of polymethyl methacrylate type (PMMA or Micropearl® M310), talc, silica/$TiO_2$ or silica/zinc oxide composites, polyethylene powders, starch powders, polyamide powders, styrene/acrylic copolymer powders, silicone elastomers, and mixtures thereof.

Preferably, these matting agents or soft-focus effect fillers are used in a proportion from 0.1% to approximately 10% by weight, relative to the total weight of the composition, preferably in a proportion of from 0.1% to approximately 7% by weight;

one or more coated or uncoated, mineral and/or organic, nacreous or non-nacreous, white or colored pigments insoluble in the medium, intended to color and/or opacify the composition. They may be of usual or nanometric size. Among the mineral pigments, mention may be made of optionally surface-treated titanium dioxide, iron oxides or chromium oxides, manganese violet, ultramarine blue, chromium hydrate and ferric blue. Among the organic pigments, mention may be made of carbon black, pigments of D&C type, and lakes based on cochineal carmine of barium, strontium, calcium or aluminum. Nacreous pigments or nacres are iridescent particles which reflect light. These nacreous pigments can be chosen from white nacreous pigments such as titanium-coated mica, or bismuth oxychloride-coated mica, and colored nacreous pigments such as titanium mica with iron oxides. The pigments may have undergone a surface treatment. Preferably, these pigments are used in a proportion of from 0.1% to approximately 10% by weight, relative to the total weight of the composition, preferably in a proportion of from 0.1% to approximately 5% by weight;

one or more tensioning agents. The term "tensioning agent" should be understood to mean a compound suitable for tensioning the skin and, by virtue of this tensioning effect, smoothing the skin and immediately reducing or causing to disappear the wrinkles and fine lines thereof. As tensioning agents, mention may be made of polymers of natural origin; mixed silicates; colloidal particles of inorganic fillers; synthetic polymers; and mixtures thereof. Mention may in particular be made of: polymers of plant or microbial origin, polymers derived from integuments, egg proteins and latexes of natural origin. These polymers are preferably hydrophilic. As polymers of plant origin, mention may in particular be made of proteins and protein hydrolyzates, and more particularly extracts of cereals, of leguminous plants and of oil-producing plants, such as extracts of corn, of rye, of wheat, of buckwheat, of sesame, of spelt, of pea, of tapioca, of bean, of lentil, of soya and of lupin. Other tensioning agents that can be used according to the invention are polysaccharides of natural origin, in particular starch derived in particular from rice, from corn, from tapioca, from potato, from cassava, from pea; carrageenans, acacia gums (gum Arabic), alginates, agars, gellans, xanthan gums, cellulose-based polymers and pectins, advantageously as an aqueous dispersion of gel microparticles, cellulose-based derivatives, and mixtures thereof. The synthetic polymers are generally in the form of a latex or of a pseudo latex and may be of polycondensate type or obtained by radical polymerization. Mention may in particular be made of polyester/polyurethane and polyether/polyurethane dispersions. Preferably, the tensioning agent is a copolymer of PVP/dimethiconyl acrylate and of hydrophilic polyurethane (Aquamere® S-2011° from the company Hydromer);

one or more preservative(s);

sequestrant agents such as EDTA salts;

fragrances;

and mixtures thereof.

Examples of such adjuvants are mentioned in particular in the CTFA Dictionary (International Cosmetic Ingredient Dictionary and Handbook published by The Cosmetic, Toiletry and Fragrance Association, 11th edition, 2006) which describes a large variety, without limitation, of cosmetic and pharmaceutical ingredients normally used in the skincare industry, which are suitable for use as additional ingredients in the compositions according to the present invention.

Those skilled in the art are able to choose, from all of these optional additives, both the composition and the amount of those that will be added to the composition, such that said composition retains all of its properties.

In addition, the composition according to the present invention can optionally contain various active agents which can be chosen from the group consisting of vitamins, antioxidants, moisturizing agents, anti-pollution agents, keratolytic agents, astringents, anti-inflammatories, bleaching agents and agents for promoting the microcirculation. Preferably, the composition comprises at least one active agent chosen from moisturizing agents, antioxidants, agents for promoting the microcirculation, and mixtures thereof.

Examples of vitamins include vitamins A, B1, B2, B6, C and E and derivatives thereof, pantothenic acid and derivatives thereof and biotin.

Examples of antioxidants include ascorbic acid and derivatives thereof, such as ascorbyl palmitate, ascorbyl tetraisopalmitate, ascorbyl glucoside, magnesium ascorbyl phosphate, sodium ascorbyl phosphate and ascorbyl sorbate; tocopherol and derivatives thereof, such as tocopheryl acetate, tocopheryl sorbate and other tocopherol esters; BHT and BHA; esters of gallic acid, phosphoric acid, citric acid, maleic acid, malonic acid, succinic acid, fumaric acid, cephalin, hexametaphosphate, phytic acid, and extracts of plants, for example of roots of *Zingiber officinale* (ginger), such as the Blue *Malagasy* Ginger sold by the company Biolandes, of *Chondrus crispus*, *Rhodiola*, *Thermus thermophilus*, maté leaf, oak wood, kayu rapet bark, sakura leaves and ylang ylang leaves.

Examples of moisturizing agents include polyethylene glycol, propylene glycol, dipropylene glycol, glycerol, butylene glycol, xylitol, sorbitol, maltitol, mucopolysaccharides, such as chondroitin sulfuric acid, hyaluronic acid of high or low molecular weight or else hyaluronic acid potentiated with a silanol derivative, such as the active agent Epidermosil® sold by the company Exymol, and mucoitin sulfuric acid; caronic acid; atelocollagen; chloresteryl 12-hydroxystearate; biliary salts, a principal component of NMF (natural moisturizing factor) such as a salt of pyrrolidonecarboxylic acid and a salt of lactic acid, an amino acid analog such as urea, cysteine and serine; a short-chain soluble collagen, diglycerol PPGs, homo- and copolymers of 2-meth-acryloyloxyethylphosphorylcholine such as Lipidure HM and Lipidure PBM from NOF; allantoin; glycerol derivatives such as PEG/PPG/polybutylene glycol-8/5/3 glycerol from NOF sold under the trade name Wilbride®S753 or else the glyceryl polymethacrylate from Sederma sold under the trade name Lubragel®MS; the trimethylglycine sold under the trade name Aminocoat® by the company Ashahi Kasei Chemicals and various plant extracts, such as extracts of *Castanea sativa*, hydrolyzed hazelnut proteins, *Tuberosa polyanthus* polysaccharides, Argania *spinosa* kernel oil and extracts of nacre containing a conchiolin, which are sold in particular by the company Maruzen (Japan) under the trade name Pearl Extract®.

Other examples of moisturizing agents include compounds which stimulate the expression of the matriptase MT/SP1, such as an extract of locust bean pulp, and also agents which stimulate the expression of CERT, of ARNT2 or of FN3K or FN3K RP; agents which increase keratinocyte proliferation or differentiation, either directly, or indirectly by stimulating for example the production of β-endorphins, such as extracts of *Thermus thermophilus* or of *Theobroma cacao* bean shells, water-soluble corn extracts, peptide extracts of Voandzeia *subterranea* and niacinamide; epidermal lipids and agents which increase epidermal lipid synthesis, either directly, or by stimulating certain β-glucosidases which modulate the deglycosylation of lipid precursors, for instance glucosylceramide to ceramides, such as phospholipids, ceramides, or lupin protein hydrolyzates, and dihydrojasmonic acid derivatives.

Examples of anti-pollution agents include Moringa pterygosperma seed extract (for example Purisoft® from LSN); Shea butter extract (for example Detoxyl® from Silab), and a mixture of ivy extract, phytic acid and sunflower seed extract (for example Osmopur® from Sederma).

Examples of keratolytic agents include α-hydroxy acids (for example glycolic, lactic, citric, malic, mandelic or tartaric acids) and β-hydroxy acids (for example salicylic acid), and esters thereof, such as $C_{12-13}$ alkyl lactates, and plant extracts containing these hydroxy acids, such as *Hibiscus sabdriffa* extracts.

Examples of astringents include *hamamelis* extracts.

Examples of anti-inflammatories include bisabolol, allantoin, tranexamic acid, zinc oxide, sulfur oxide and derivatives thereof, chondroitin sulfate, and glycyrrhizic acid and derivatives thereof such as glycyrrhizinates.

Examples of bleaching agents include arbutin and derivatives thereof, ferulic acid (such as Cytovector®: water, glycol, lecithin, ferulic acid, hydroxyethylcellulose, sold by BASF) and derivatives thereof, kojic acid, resorcinol, lipoic acid and derivatives thereof, such as resveratrol diacetate monolipoate as described in patent application WO 2006/134282, ellagic acid, leucodopachrome and derivatives thereof, vitamin B3, linoleic acid and derivatives thereof, ceramides and homologs thereof, a peptide as described in patent application WO 2009/010356, a bioprecursor as described in patent application WO 2006/134282 or a tranexamate salt such as the hydrochloride salt of cetyl tranexamate, a licorice extract (*Glycyrrhiza glabra* extract), which is sold in particular by the company Maruzen under the trade name Licorice Extract®, a bleaching agent that also has an antioxidant effect, for instance vitamin C compounds, including ascorbate salts, ascorbyl esters of fatty acids or of sorbic acid, and other ascorbic acid derivatives, for example ascorbyl phosphates, such as magnesium ascorbyl phosphate and sodium ascorbyl phosphate, or sorbic acid saccharide esters, which include, for example, ascorbyl-2-glucoside, 2-O-alpha-D-glucopyranosyl L-ascorbate or 6-O- beta-D-galactopyranosyl L-ascorbate. An active agent of this type is sold in particular by the company DKSH under the trade name Ascorbyl Glucoside®.

Examples of agents which promote the microcirculation include an extract of lupin (such as Eclaline® from Silab), of ruscus, of horse chestnut, of ivy, of *ginseng* or of sweet clover, caffeine, nicotinate and derivatives thereof, a *Corallina officinalis* algal extract such as that sold by CODIF; and mixtures thereof. These agents which are active on skin microcirculation can be used to prevent dulling of the complexion and/or to improve the uniformity and the radiance of the complexion.

The composition used according to the invention can also comprise, in addition to a *Camellia japonica* flower extract, at least one active agent chosen from: agents which stimulate tensin 1 expression, such as an elemi extract; agents which stimulate FN3K expression and/or FN3K RP expression, such as a *Butea frondosa* extract; agents which stimulate CERT or ARNT2 expression; agents which stimulate growth factor production; anti-glycation or deglycating agents; agents which increase collagen synthesis or which prevent collagen degradation (anti-collagenase agents, in particular matrix metalloproteinase inhibitors), in particular agents which increase collagen IV and/or hyaluronan and/or fibronectin synthesis, such as at least one acylated oligopeptide, in particular that sold by the company Sederma under the trade name Matrixyl® 3000; agents which increase elastin synthesis or prevent elastin degradation (anti-elastase agents); agents which increase glycosaminoglycan or proteoglycan synthesis or which prevent the degradation thereof (anti-proteoglycanase agents) such as the active agent Epidermosil® (hyaluronic acid combined with methylsilanetriol) sold by the company Exsymol; agents which stimulate integrin synthesis by fibroblasts; agents which increase fibroblast proliferation; agents which facilitate percutaneous absorption, such as alcohols, fatty alcohols and fatty acids, and ester or ether derivatives thereof, pyrrolidones, 4-alkyl-oxazolidin-2-ones, such as 4-decyloxazolidin-2-one; terpenes, essential oils and α-hydroxy acids; and mixtures thereof, without this list being limiting.

It appeared to the applicant that the combination of at least one *Camellia japonica* flower extract with one or more of the active agents described above made it possible to advantageously combine, in one and the same formula, the effects of these combinations of active agents and to thus obtain maximum and long-lasting moisturization of the skin.

The cosmetic composition according to the invention thus advantageously contains at least one *Camellia japonica* flower extract with at least one active agent chosen from moisturizing agents.

More particularly, it can contain at least one active agent chosen from: a fermented extract of *Thermus thermophilus*; an extract of *Zingiber officinale* (ginger) root; hyaluronic acid and derivatives thereof; an extract of locust bean pulp; and mixtures thereof.

A subject of the invention is also the cosmetic use of the *Camellia japonica* flower extract as described above or of the cosmetic composition as described above, for moisturizing and/or protecting human skin against drying out.

In this embodiment, the extract or the composition is applied to nonpathological dry skin.

The invention will now be illustrated by means of the following nonlimiting examples.

EXAMPLE 1—PREPARATION OF AN OILY EXTRACT OF *CAMELLIA JAPONICA* ALBA PLENA FLOWERS

An oily extract is prepared from 2 kg of white flowers of *Camellia japonica* Alba plena and 9 kg of refined *camellia* oil.

The freshly isolated flowers are dehydrated to a solids content of 90% and then cooled to −80° C. so as to be immediately milled in a propeller mill, at a temperature of between −30 and −80° C. A fine powder which has a particle size of between 100 and 300 µm and is uniform is obtained.

The process comprising the following steps is then carried out:

a) the flower powder and the refined *camellia* oil are introduced into a closed stainless steel reactor, which is placed under a saturated nitrogen atmosphere. The mixture is maintained at ambient temperature for approximately 24 hours, so as to ensure impregnation of the plant powder with the oil.

b) The mixture is placed in a closed reactor equipped with an ultrasound generator, under a saturated nitrogen atmosphere, and subjected to an ultrasound treatment at a frequency of 20 kHz, at ambient temperature, for 15 minutes.

c) The mixture is placed in a closed reactor equipped with a stirrer and under a saturated nitrogen atmosphere, then subjected to a microwave treatment, under a power of 0.4 kW/kg mixture for a period of 7 min. The maximum temperature reached is 118° C.

Steps b) and c) are repeated twice successively. Between each step, the mixture is cooled to ambient temperature for 3 h under a saturated nitrogen atmosphere.

The mixture thus obtained is subjected to centrifugation at 5000 revolutions/min for 15 minutes, at a temperature of 40° C., on a filtering cloth with a porosity of 5 µm, in order to separate the oily fraction (oily extract) from the solid matter (fatty cake) and to obtain a homogeneous liquid extract.

After a return to ambient temperature, the oily extract obtained is in the form of a homogeneous fluid oil which has a light yellow color and a weak floral odor. In each case, the oily extract obtained has a water content less than 0.2 g/100 g, an oleic acidity of less than or equal to 0.4% and a peroxide number of less than 3 meq $O_2$/kg.

EXAMPLE 2—TEST FOR STIMULATION OF KRT2 GENE EXPRESSION ON KERATINOCYTES TREATED WITH A *CAMELLIA JAPONICA* FLOWER EXTRACT OBTAINED IN EXAMPLE 1

Protocol:

The effects of the extract of example 1 or of the refined *camellia* oil sold by the company Ardex were evaluated by real-time PCR (RT-PCR), for the purpose of quantifying the expression of the keratin 2 (KRT2) gene in a treated sample compared with a nontreated control sample.

The results were expressed as percentage increase or decrease in expression of the target gene (KRT2) in the treated sample. The results are standardized with respect to the expression of the same gene in the nontreated control sample, which is fixed at 100%.

Specifically, the test was carried out on normal human keratinocytes cultured to post-confluencing and then optionally treated for 24 hours, in triplicate. The keratinocytes come from two independent donors.

The mRNA was isolated using the RNeasy kit (Qiagen) and quantified using the QuantIT Ribogreen kit (Invitrogen) according to the producer's recommendations. The reverse transcription into cDNA was carried out using the iScript Reverse Transcription SuperMix kit (Biorad) also according to the producer's recommendations.

The quantitative real-time PCR measurement was carried out using the iCYCLER IQ machine (Biorad), the Taqman probes specific for the KRT2 gene and the beta-2-microglobulin gene (reference gene) (Applied Biosystems) and the IQ Supermix (BioRad).

Results:

TABLE 1

|  | Concentration[1] | Stimulation of KRT2 expression (%) |
|---|---|---|
| Nontreated keratinocytes | — | 100 |
| Camellia japonica flower extract according to example 1 | 0.025% | 170 |
| Refined camellia oil sold by the company Ardex | 0.025% | 93 |

[1]the concentrations of the extracts are expressed by weight of crude extract per weight of preparation (the extract obtained according to example 1 being diluted in the culture medium for keratinocyte growth)

The *Camellia japonica* flower extract stimulates the expression of the KRT2 mRNA compared with the nontreated control and compared with the comparative sample treated with a refined *camellia* oil obtained by means of a process (i.e. that of the company Ardex) other than that of the present application.

EXAMPLE 3: COSMETIC COMPOSITION (O/W SERUM)

The following composition can be prepared in a manner that is conventional for those skilled in the art. The amounts indicated below are expressed as weight percentages. The ingredients in uppercase letters are identified in accordance with the INCI name.

| INCI name | % (weight/weight) |
|---|---|
| WATER | QS 100.00 |
| Chelating agent | 0.05 |
| pH adjuster | 0.05 |
| Preservative | 0.05 |
| Glycol | 3.25 |
| AMMONIUM ACRYLOYLDIMETHYLTAURATE/VP COPOLYMER | 1.20 |
| ACRYLATES/C10-30 ALKYL ACRYLATE CROSSPOLYMER | 0.20 |
| GLYCERIN | 3.00 |
| GLYCERYL POLYMETHACRYLATE | 4.18 |
| SODIUM ACETYLATED HYALURONATE | 0.05 |
| PEG/PPG/POLYBUTYLENE GLYCOL-8/5/3 GLYCERIN | 2.00 |
| SODIUM PCA | 3.00 |
| Oil | 10.00 |
| ALCOHOL | 8.00 |
| FRAGRANCE | 0.30 |
| ZINGIBER OFFICINALE (GINGER) ROOT EXTRACT [1] | 0.10 |
| HYALURONIC ACID & SILANETRIOL & CITRIC ACID [2] | 5.00 |
| OLEOACTIF CAMELIA BLANC [3] | 0.10 |
| CROSSLINKED POLYMETHYLMETHACRYLATE [4] | 0.75 |
| HDI/TRIMETHYLOL HEXYLLACTONE | 0.75 |
| CROSSPOLYMER & SILICA [5] | |
| Locust bean pulp extract | 0.10 |

[1] Blue Malagasy Ginger ® sold by the company Biolandes
[2] Epidermosil ® sold by the company Exsymol
[3] as described in example 1
[4] Micropearl ® M310 from SEPPIC
[5] Plastic Powder ® D-400/BPD-500 ® from Kobo This composition can be applied daily, in the morning and/or evening, to skin that is particularly dehydrated and/or exposed to environmental attacks, in order to improve the comfort thereof and to make the complexion uniform.

EXAMPLE 4: COSMETIC COMPOSITION (O/W SERUM)

The following composition can be prepared in a manner that is conventional to those skilled in the art. The amounts indicated below are expressed as weight percentages. The ingredients in uppercase letters are identified in accordance with the INCI name.

| INCI name | % (weight/weight) |
|---|---|
| WATER | QS 100.00 |
| Chelating agent | 0.05 |
| pH adjuster | 0.05 |
| Preservative | 0.05 |
| Glycol | 15.00 |
| CARBOMER | 0.08 |
| ACRYLATES/C10-30 ALKYL ACRYLATE CROSSPOLYMER | 0.17 |
| GLYCERIN | 15.00 |
| DIPENTAERYTHRITYL HEXACAPRYLATE/HEXACAPRATE | 4.3 |
| ISONONYL ISONONANOATE | 4.3 |
| FRAGRANCE | 0.30 |
| PVP | 0.095 |
| AMODIMETHICONE | 0.04 |
| ZINGIBER OFFICINALE (GINGER) ROOT EXTRACT[1] | 0.10 |
| OLEOACTIF CAMELIA BLANC[2] | 0.1 |
| SODIUM HYALURONATE | 0.01 |

[1]Blue Malagasy Ginger ® sold by the company Biolandes
[2]as described in example 1

This composition can be applied daily, in the morning and/or evening, to skin that is particularly dehydrated and/or exposed to environmental attacks, in order to improve the comfort thereof and to make the complexion uniform.

The invention claimed is:

1. A *Camellia japonica* flower extract obtainable by means of an extraction process comprising the following steps:
   a) mixing and impregnating a *Camellia japonica* flower powder with a fatty substance or a fatty substance mixture at a temperature above the melting point of said fatty substance or of said mixture and under an atmosphere free or essentially free of oxygen,
   b) dispersing of the *Camellia japonica* flower powder in the fatty substance or said fatty substance mixture at a temperature above the melting point of said fatty substance or of said mixture, under an atmosphere free or essentially free of oxygen, to make a microdispersion, c) heating the mixture thus obtained at a temperature between 60 and 180° C. for a period of between 1 and 10 minutes, under an atmosphere free or essentially free of oxygen, wherein step c) be may be carried out before, during or after step b).

2. The extract as claimed in claim 1, wherein the *camellia* flower comes from the variety *Camellia japonica* Alba plena.

3. The extract as claimed in claim 1, wherein the ratio between the *Camellia japonica* flower powder and the fatty substance in step a) is between 1:0.5 and 1:20, said ratio being expressed by weight/weight of fatty substance or by weight/volume of fatty substance.

4. The extract as claimed in claim 1, wherein the fatty substance(s) is a plant oil that is liquid at ambient temperature, a plant butter having a melting point of between 25 and 40° C., or a plant wax having a melting point above 40° C.

5. The extract as claimed in claim 1, wherein step a) is carried out at a temperature above the melting point of the fatty substance or of the fatty substance mixture used, the temperature being between this melting point and the melting point +20° C., for a period of between 1 and 48 hours.

6. The extract as claimed in claim 1, wherein step b) comprises a treatment by ultrasonic cavitation, for a period of between 2 and 30 minutes, at a cavitation frequency of less than 100 kHz.

7. The extract as claimed in claim 1, wherein step b) is carried out at ambient temperature or at a temperature above the melting point of the fatty substance or fatty substance mixture used.

8. The extract as claimed in claim 1, wherein step c) is carried out at a temperature of between 100 and 150° C., for a period ranging from 1 to 10 minutes.

9. The extract as claimed in claim 8, wherein the temperature of step c) is obtained by means of a microwave treatment having a working power ranging from 500 to 10 000 watts per kilogram of mixture.

10. The extract as claimed in claim 1, wherein the *Camellia japonica* flower powder is provided in the form of a dispersible product obtained by milling at a temperature between −20 and −80° C.

11. The extract as claimed in claim 1, wherein steps a), b) and/or c) are advantageously carried out in the absence of light or of any oxidizing radiation.

12. The extract as claimed in claim 1, wherein steps b) and c) are carried out n times; thus corresponding to steps bn) and cn), n corresponding to the total number of repetitions of the cycle {(step a)+(step b)+(step c)}, n being at least equal to 2.

13. A cosmetic composition containing, in a physiologically acceptable medium, at least one *Camellia japonica* flower extract as claimed in claim 1.

14. The composition as claimed in claim 13, further comprising at least one active agent chosen from moisturizing agents, antioxidants, agents promoting the microcirculation, and mixtures thereof.

15. The composition as claimed in claim 13, wherein the active agent is chosen from: a fermented extract of *Thermus thermophilus*; an extract of *Zingiber officinale* root; hyaluronic acid and derivatives thereof; an extract of locust bean pulp; and mixtures thereof.

16. A method for moisturizing and/or protecting human skin against drying out, comprising applying an effective amount of the *Camellia japonica* flower extract as claimed in claim 1.

17. The method of claim 16, wherein in the extract or the composition is applied to nonpathologically dry skin.

18. The extract as claimed in claim 1, wherein the ratio between the *Camellia japonica* flower powder and the fatty substance in step a) is between 1:19 and 1:1, said ratio being expressed by weight/weight of fatty substance or by weight/volume of fatty substance.

19. The extract as claimed in claim 1, wherein the ratio between the *Camellia japonica* flower powder and the fatty substance in step a) is between 1:9 and 1:3, said ratio being expressed by weight/weight of fatty substance or by weight/volume of fatty substance.

20. The extract as claimed in claim 4, wherein the fatty substance(s) is an oil chosen from *camellia* oil, rapeseed oil, sunflower oil, olive oil, sesame oil, apricot kernel oil, grape seed oil, sweet almond oil, safflower oil, hazelnut oil, argon oil, rose musk oil, evening primrose oil, borage oil, jojoba liquid wax, and mixtures thereof.

* * * * *